(12) United States Patent
Paul

(10) Patent No.: US 6,448,303 B1
(45) Date of Patent: Sep. 10, 2002

(54) HOT MELT ADHESIVES FOR DERMAL APPLICATION

(75) Inventor: Charles W. Paul, Madison, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 09/752,260

(22) Filed: Dec. 29, 2000

(51) Int. Cl.$^7$ .................................................. C08L 5/04
(52) U.S. Cl. ...................... 523/105; 523/111; 523/113; 424/448; 424/449
(58) Field of Search ................... 523/111, 105; 526/318.1, 318.4, 318.5, 931, 935; 427/208.4; 424/448, 449

(56) References Cited

U.S. PATENT DOCUMENTS

| 4,259,470 | A | * | 3/1981 | Trotter et al. ................ 526/348 |
| 5,306,502 | A | * | 4/1994 | Jaeger et al. ................ 424/443 |
| 5,559,165 | A | * | 9/1996 | Paul ............................ 523/111 |
| 5,965,154 | A | * | 10/1999 | Haralambopoulos ........ 424/449 |

* cited by examiner

*Primary Examiner*—Edward J. Cain
*Assistant Examiner*—James T. Yeh
(74) *Attorney, Agent, or Firm*—Cynthia L. Foulke

(57) ABSTRACT

A pressure sensitive hot melt adhesive composition which comprises a high molecular weight rubber and less than about 60 parts by weight of a liquid diluent, and has a G' of less than about $15 \times 10^4$ dynes/cm$^2$ at 10 rad/s at 25° C. is useful for adhesive skin application (e.g., surgical tape), including transdermal drug delivery applications.

20 Claims, No Drawings

HOT MELT ADHESIVES FOR DERMAL APPLICATION

FIELD OF THE INVENTION

The invention relates to an adhesive composition. In particular, a hot melt pressure-sensitive adhesive for dermal applications.

BACKGROUND OF THE INVENTION

Adhesives for application to the skin are permanently tacky at room temperature, hold the adhered article to the skin with gentle pressure, and should be easily removed without causing pain or depositing adhesive residue. Useful adhesives need to adhere well to human skin during perspiration, when the weather is hot, or in an environment of draining wounds.

Painless removal of adhesive articles from hair-covered regions of skin is especially difficult. For such regions, a soft adhesive with minimal viscoelastic loss is required. Hydrogels have been used effectively for such purposes, but have their own disadvantages, including high price, special packaging and release layers to retain the moisture (typically about 40% of the total adhesive), as well as variations in properties during use in response to changes in humidity.

Commonly assigned U.S. Pat. No. 5,559,165 improved upon the state of the art by providing a hot melt pressure sensitive adhesive having the desirable characteristics of a hydrogel, but not the drawbacks associated with their use. While U.S. Pat. No. 5,559,165 represents a substantial contribution to the art, there continues to be a need for improvements and modifications in hot melt adhesives for use in dermal applications, in particular hot melt adhesives which leave no residue upon removal from the skin.

SUMMARY OF THE INVENTION

The invention provides a hot melt pressure sensitive adhesive especially suited for adhesive skin application, including transdermal drug delivery applications. The invention is based on the discovery that hot melt pressure sensitive adhesives formulated with higher mid-block Tg's and less liquid diluent, in particular less liquid tackifier, than conventional hot melt pressure sensitive adhesives heretofore known and used in the art give good skin adhesion and leaves less adhesive residue on the skin.

One aspect of the invention is directed to a pressure sensitive hot melt adhesive composition. The adhesive comprises high molecular weight rubber and less than about 60 parts by weight, more preferably from about 35 to about 55 parts by weight, based on the total weight of the composition, of a liquid diluent. Preferred adhesive compositions of the invention comprise from about 1 to about 20 parts by weight of a high molecular weight rubber triblock or radial block copolymer, from 0 to about 20 parts by weight of a high molecular weight diblock rubber, 0 to about 10 parts by weight of other compatible high molecular weight polymers, 0 to about 30 parts by weight of an end block resin, 0 to less that about 60 parts by weight oil or other liquid midblock diluent, 0 to about 60 parts by weight of a solid tackifier and 0 to about 3 parts by weight of an anti-oxidant.

Another aspect of the invention is directed to a transdermal drug delivery system comprising a pressure sensitive hot melt adhesive and a therapeutic agent. The agent, while physiologically active, may or may not be pharmaceutically active. In one embodiment, the adhesive serves as a carrier for the physiologically active agent.

Still another aspect of the invention is directed to a transdermal drug delivery system comprising an adhesive layer, a therapeutic agent and a backing layer. In one embodiment, the drug delivery system also comprises a release layer. In another embodiment of the drug delivery system the drug to be delivered is incorporated into the adhesive.

Yet another aspect of the invention is directed to a method of administering a therapeutic agent to a patient comprising applying to a body surface of the patient a transdermal drug delivery system comprising a pressure sensitive hot melt adhesive and a physiologically active agent.

DETAILED DESCRIPTION OF THE INVENTION

The disclosures of all documents cited herein are incorporated in their entireties by reference.

As used herein, the term "pressure-sensitive adhesive" refers to a viscoelastic material which adheres instantaneously to most substrates with the application of slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives.

Preferred adhesives will generally have a midbock Tg of from about −30° C. to about room temperature, more preferable from about −30° C. to about 10° C. Useful adhesives will preferably have a G' (storage modulus) less than about $15 \times 10^4$ dynes/cm$^2$ at 10 rad/s. (25° C.), preferably at least about $1 \times 10^4$ and most preferably from about 4 to $10 \times 10^4$ dynes/cm$^2$. Low G' provides a soft adhesive that easily wets at rough surfaces such as skin. The adhesives will also preferable have a G" (loss modulus) of about 1 to $6 \times 10^4$ dynes/cm$^2$. It has been found that maintaining G" within this range ensures adequate hold while ensuring painless removal. A tensile strength greater than 10 psi is necessary to ensure that the adhesive does not fail cohesively upon removal.

As used herein the term "high molecular weight rubbers" are those having a viscosity at 25° C. of above 1,000 cP in toluene at a concentration of 20% by weight.

In the case of the high viscosity triblock copolymers employed herein, they may have the more general configuration A-B-A wherein the polymer blocks A are non-elastomeric polymer blocks which, as homopolymers have glass transition temperatures above 20° C., while the elastomeric polymer blocks B are isoprene, or butadiene which may be partially or substantially hydrogenated or mixtures thereof. Further, the copolymers may be linear or branched. Typical branched structures contain an elastomeric portion with at least three branches which can radiate out from a central hub or can be otherwise coupled together. The amount of the triblock component is preferably from about 1 to about 20 parts by weight, more preferably about 3 to about 8 parts by weight.

The non-elastomeric blocks may comprise homopolymers or copolymers of vinyl monomers such as vinyl arenes, vinyl pyridines, vinyl halides and vinyl carboxylates, as well as acrylic monomers such as acrylonitrile, methacrylonitrile, esters of acrylic acids, etc. Monovinyl aromatic hydrocarbons include particularly those of the benzene series such as styrene, vinyl toluene, vinyl xylene, ethyl vinyl benzene as well as dicyclic monovinyl compounds such as vinyl naphthalene and the like. Other non-elastomeric polymer blocks may be derived from alpha olefins, alkylene oxides, acetals, urethanes, etc. Styrene is preferred.

The elastomeric block component making up the remainder of the copolymer is isoprene or butadiene which may be hydrogenated as taught, for example, in U.S. Pat. No. 3,700,633. This hydrogenation of butadiene may be either partially or substantially complete. Selected conditions may be employed for example to hydrogenate the elastomeric butadiene block while not so modifying the vinyl arene polymer blocks. Other conditions may be chosen to hydrogenate substantially uniformly along the polymer chain, both the elastomeric and non-elastomeric blocks thereof being hydrogenated to practically the same extent, which may be either partial or substantially complete. Hydrogenated polymers are preferred to minimize degradation during processing, which is a more severe problem with higher molecular weight polymers.

The high viscosity triblock copolymer of the invention can have a broad range of non-elastomeric end block to elastomeric center block ratio of approximately about 5:95 or less to about 40:60 or higher. Examples of high viscosity triblock copolymers that can be utilized to achieve one or more of the novel properties of the present invention are styrene-ethylene-butylene-styrene block copolymers (SEBS) available from Shell Chemical Company and Pecten Chemical Company under trade designations Kraton G 1651, Kraton G 1654, Kraton G 4600, Kraton G 4609 and the like. Other grades of (SEBS) polymers can also be utilized in the present invention provided such SEBS polymers exhibits the required high viscosity. Such SEBS polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C. Although the typical ratio values for Kraton G 1651, 4600, and 4609 are approximately about 33:67 and for Kraton G 1855X approximately about 27:73, as noted previously, these ratios can vary broadly from the typical product specification values.

It is preferred that the adhesive additionally contain up to 20, preferably 3 to 8, parts by weight of a high molecular weight (i.e., viscosity>1000 cps at 25° C. at 20% in toluene) diblock polymer of the general A-B configuration where A and B are as described previously. Preferred are Kraton G 1701X or 1702X which are both styrene ethylene propylene diblock polymers. Kraton G1702X is most preferred While the adhesive formulation preferably contains some diblock polymer, the diblock may be replaced entirely or in part with another high molecular weight polymer that is compatible with the system. For example, polyisobutylene (e.g., Vistanex from Exxon), polyisoprene (e.g., from Kuraray), or styrene/butadiene copolymer (e.g., Plioflex from Goodyear) may be used in amounts of about 2 to 10 parts by weight.

As will be described hereinbelow, various additives are known to associate with the particular blocks (domains) of the block polymer(s), altering the behavior of those portions accordingly. In more detail, the mid-block portion or domain (i.e., the "B-block") of the polymer needs to have a Tg less than about room temperature. As other mid-block compatible components such as plasticizing oils and tackifiers are added, these components associate with the B domains swelling them and generally resulting in a change in the Tg thereof. For most pressure sensitive adhesive applications, a Tg in the range of about 0° C. to 25° C., preferably about 15° C. is desirable; however, for use herein mid-block Tg ranges from −30° C. up to about 10° C., more preferably from about −20° C. to about 0° C. are required.

The practice of the invention, the amount of liquid diluents is less than about 60 parts by weight. In a preferred embodiment, the majority of the liquid diluent is oil. Preferable any liquid diluent used is an oil diluent. A useful diluent is primarily aliphatic in character and is compatible with the polymer midblock. Included in these materials are plasticizers such as paraffinic and naphthenic petroleum oils, highly refined aromatic-free paraffinic and naphthenic food and technical grade white petroleum mineral oils, and liquid tackifiers such as the synthetic liquid oligomers of polybutene, polypropene, polyterpene, etc. The synthetic series process oils are high viscosity oligomers which are permanently fluid liquid monolefins, isoparaffins or paraffins of moderate to high molecular weight. Liquid plasticizing or tackifying diluents include polyterpenes such as Wingtack 10 available from Goodyear, and Escorez 2520 based on a C5 feed stream available from Exxon Chemical. Other liquid diluents would include polyisoprene, available as LIR 50 from Kuraray, Amoco's polybutenes available under the name Indopol. Most preferred are white paraffinic oils.

There may also be present up to 60 parts, preferably 30 to 50 parts by weight of a solid tackifier (i.e., one having a Ring and Ball softening point above 25° C.) which is compatible with the midblock. Suitable tackifiers include any compatible resins or mixtures thereof such as (1) natural or modified rosins such, for example, as gum rosin, wood rosin, tall-oil rosin, distilled rosin, hydrogenated rosin, dimerized rosin, and polymerized rosin; (2) glycerol and pentaerythritol esters of natural or modified rosins, such, for example as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natural terpenes, e.g., styrene/terpene and alpha methyl styrene/terpene; (4) polyterpene resins having a softening point, as determined by ASTM method E28,58T, of from about 80° to 150° C.; the latter polyterpene resins generally resulting from the polymerization of terpene hydrocarbons, such as the bicyclic monoterpene known as pinene, in the presence of Friedel-Crafts catalysts at moderately low temperatures; also included are the hydrogenated polyterpene resins; (5) phenolic modified terpene resins and hydrogenated derivatives thereof, for example, as the resin product resulting from the condensation, in an acidic medium, of a bicyclic terpene and phenol; (6) aliphatic petroleum hydrocarbon resins having a Ball and Ring softening point of from about 70° to 135° C.; the latter resins resulting from the polymerization of monomers consisting of primarily of olefins and diolefins; also included are the hydrogenated aliphatic petroleum hydrocarbon resins; (7) alicyclic petroleum hydrocarbon resins and the hydrogenated derivatives thereof; and (8) aliphatic/aromatic or cycloaliphaticlaromatic copolymers and their hydrogenated derivatives.

Preferred tackifiers for use herein include polyterpenes such as Piccolyte A125 from Hercules; aliphatic resins such as Wingtack 95 from Goodyear; cycloaliphatic resins such as Eastotac H100 from Eastman; and aliphatic/aromatic or cycloaliphatic/aromatic resins such as ECR 149B or ECR 179A from Exxon Chemical. Most preferred are the aliphatic or cycloaliphatic resins while the least desirable are the rosin esters or phenolic modified polyterpenes are least preferred.

The desirability and selection of the particular tackifying agent is, in large part, dependent upon the specific block copolymer employed.

Additionally, it may be desirable to incorporate in the adhesive up to 30 parts by weight of an end block resin. End block resins are those resins which reside predominantly in the non-elastomer domains of the rubber after the adhesive is cooled. Representative of such resins are the primarily aromatic resins based on mixed C9 petroleum distillation streams such as the Picco materials available from Hercules, or resins based on pure or mixed monomer streams of aromatic monomers such as homo or copolymers of vinyl toluene, styrene, alpha-methyl styrene, coumarone or indene. Preferred are those based on alpha-methyl styrene available from Hercules under the Kristalex trade name. If present, the end block resin is generally used in an amount of 5 to 30 parts by weight, preferably less than 20 parts.

Optionally there may also be present 0 to 5% by weight of a wax component such as the polyethylene waxes available from Allied-Signal under the A-C symbol. If used, the wax is generally present in an amount of at least 2 parts by weight.

Finally, antioxidants typically used in the production of rubber based pressure sensitive adhesives may be present in an amount up to about 3 parts by weight. Among the applicable stabilizers or antioxidants utilized herein are included high molecular weight hindered phenols and multifunctional phenols such as sulfur and phosphorous-containing phenols. Hindered phenols are well known to those skilled in the art and may be characterized as phenolic compounds which also contain sterically bulky radicals in close proximity to the phenolic hydroxyl group hereof. In particular, tertiary butyl groups generally are substituted onto the benzene ring in at least one of the ortho positions relative to the phenolic hydroxy group. The presence of these sterically bulky substituted radicals in the vicinity of the hydroxyl group serves to retard its stretching frequency and, correspondingly, its reactivity; this steric hindrance thus providing the phenolic compound with its stabilizing properties. Representative hindered phenols include: 1,3,5-trimethyl 2,4,6-tris(3,5-di-tert-butyl-4-hydroxybenzyl) benzene; pentaerythrityl tetrakis-3(3,5-di-tert-butyl-4-hydroxyphenyl)-propionate; 4,4'-methylenebis(2,6-tert-butylphenol); 4,4'-thiobis(6-tert-butyl-o-cresol); 2,6-di-tert-butylphenol; 6-(4-hydroxyphenoxy)-2,4-bis(n-octylthio)-1, 2,5-triazine; di-n-octadecyl 3,5-di-tert-butyl-4-hydroxybenzyl phosphonate; 2-(n-octylthio)ethyl 3,5-di-tert-butyl-4-hydroxybenzoate; and sorbitol hexa[3-(3,5-di-tert-butyl-4-hydroxyphenyl)-propionate].

As was noted above, there are a variety of ways to formulate the particular raw materials in order to obtain an adhesive having the desired midblock Tg, G' and G" values. Moreover, the particular end use for which the adhesive is intended will also affect the choice of materials and the ultimate Tg, G' and G" values. In general, it has been found that the triblock rubber provides the set of the adhesive into a gelatinous solid, while the diblock rubber improves the tack of the formulation. The end block resin provides strength to the adhesive formulation while lowering its melt viscosity by reducing the self-association of the rubber end blocks when molten. In formulating the adhesives, predominately liquid diluents are used to ensure a low Tg for the matrix (midblock portion) of the formulation. A low Tg leads to fast polymer relaxation times which in turn lead to low pain upon removal of the adhesive.

Using the above parameters as guidelines, it has been found that particularly preferred adhesives may be prepared from about 10 parts of polymer, equally split between triblock and diblock, preferably Kraton G 1651 and Kraton G1702, respectively. These rubbers are used in combination with 5 to 30 parts, preferably 10–20 parts of end block resin, with Kristalex α-methyl styrene resins most preferred. The remainder of the product is diluent and tackifier. The lower the blend Tg of the remainder, the less tack and lower peel the adhesive will exhibit. A particularly preferred hot melt adhesive composition comprises 3 to 8 parts of the triblock polymer, 3 to 8 parts diblock, 5 to 30 parts end block resin, the remainder (to 100 parts) comprising an oil a solid tackifier.

The resultant hot melt adhesives are useful as ostomy seals, adhesive tapes and bandages, wound drainage adhesive seals, wound dressings, as adherents for other products and the like that adhere to human skin and remain adherent even in a moist environment. The adhesive of the invention is particularly well-suited for use in transdermal applications. The pressure sensitive adhesive of the invention may be incorporated into a transdermal drug delivery device designed to deliver a therapeutically effective amount of a product to the skin of a patient, e.g., to cure a skin irritation or to deliver a therapeutically effective amount of drug across the skin of a patient.

The term transdermal refers to the use of the skin as a portal for the administration of drugs by topical application. The topically applied drug passes into and/or through the skin. The terms skin, derma and epidermis are used interchangeably herein. Thus "transdermal" is used broadly to refer to the topical administration of a drug which acts locally, i.e., at the surface or within the skin, such as, for example, a blemish patch used to treat acne, and to the topical application of a drug which acts systemically by diffusing through the skin and entering the blood stream.

The term patient is used herein to include animals, both human and non-human. Human patients include adults, children and infants. Non-human patients include companion animals such as dogs, cats and horses and livestock such as cattle and swine. Agricultural and horticultural applications are also contemplated.

The adhesive of the invention is contemplated for use in the manufacture of liquid reservoir patches and matrix patches. Matrix patches are particularly preferred embodiments since they are easier to manufacture than liquid reservoir patches and are more comfortable and convenient to wear.

Transdermal drug delivery devices of the invention comprise a carrier (such as liquid, gel, or solid matrix, or a pressure sensitive adhesive) into which the drug to be delivered is incorporated, a distal backing layer and a proximal release layer. When the patient peels the release liner from the adhesive and applies the patch, the drug partitions into the stratum corneum (outer skin layer) and permeates through the epidermis and dermis.

While the invention will be described in more detail in terms of a matrix-type patch, patches of the types described in Pfister et al., *Chemistry in Britain*, January 1991, pages 43–46, the disclosure of which is incorporated herein by reference, including liquid reservoir-type systems, are encompassed by the invention. Included are embodiments wherein the drug-containing polymeric phase is laminated to a pressure sensitive adhesive or used with an overlay adhesive or is the adhesive itself.

A matrix patch device according to the present invention is a unit dosage form of a drug composition in a polymeric carrier. The individual layers of the device include a substantially drug-impermeable distal backing layer, the aforementioned drug laden polymer carrier layer, also referred to herein as the carrier, and, before transdermal application, a substantially drug-impermeable proximal release layer or liner.

The portions of the carrier that are not in contact with the skin are covered by a backing. The distal backing layer, in use, defines the side of the patch that faces the environment, i.e., distal to the skin. The backing serves to protect the carrier and the components contained in the carrier, including the drug, from the environment by providing an impenetrable layer that prevents loss of the drug to the environment. Thus, the material chosen should be substantially impermeable to the drug. Advantageously, the backing material can be opaque to protect the drug from degradation from exposure to light. It may be desirable that the backing have a relatively high vapor transmission rate, since this results in the reduction of moisture buildup on the skin beneath the device and in a corresponding reduction in the amount of skin maceration that occurs. Conversely, to enhance drug flux, an occlusive backing may be selected. Further, the backing layer should be capable of binding to and supporting the other layers of the device, yet should be pliable to accommodate the movements of a person using the device since a stiff backing may cause mechanical irritation. In order to maintain the health of the covered skin during long term wear (e.g., for periods in excess of a day), it is also desirable that the backing have a relatively high permeability to oxygen. As the backing is in contact with the components of the carrier, including the drug and any excipients, it is important that the backing be stable to such components in order that the backing retains its structural integrity and conformability. It is also important that the backing not absorb the drug or excipients from the carrier. In connection with the preparation of certain reservoir type drug delivery devices, it is also desirable for the backing to be heat sealable at a relatively low temperature to a variety of other polymeric substrates.

Backings that have found use in drug delivery devices, and which can be used in the practice of this invention include, with or without modification, metal foils, metalized polyfoils, composite foils or films containing poytetrafluoroethylene (TEFLON®)-type materials or equivalents thereof, polyether block amide copolymers, polyurethanes, polyvinylidene chloride, nylon, silicone elastomers, rubber-based poylisobutylene styrene, styrene-butadiene and styrene-isoprene copolymers, polyethylene, polyester, and other such materials used in the art of transdermal drug delivery. Particularly preferred are thermoplastic polymers such as polyolefins, for example polyethylene and polypropylene, and polyesters such as polyethyleneterephthalate.

The proximal release liner or peelable film covers the skin-facing or proximal side of the device until the device is used. A silicone-coated film is typically used for such applications. Just prior to use of the device, the proximal release liner is removed to expose the drug-containing polymer layer for contact and adhesion to the skin surface. Thus, the proximal release liner is adapted to be removed from the device and should strip off the adhesive surface with minimal force.

In one embodiment, the release liner of a first patch also serves as the backing layer of a second patch. This design allows patches to be manufactured in a stacked format, and dispensed to the patient in this manner. The first patch is removed, and applied to the skin, with no excess waste generated for disposal.

The drug containing polymer layer is preferably a pressure-sensitive skin contact adhesive of the invention which is a pharmaceutically acceptable material that lacks functional groups containing reactive hydrogen moieties and forms no new functional groups upon storage. The adhesive of the invention, whether used as a carrier contact adhesive or overlay contact adhesive for transdermal patches is non-irritating, easy to apply, and easy to remove.

The term "drug" is to be construed herein in its broadest sense to mean any agent which is intended to produce some therapeutic benefit. The agent may or may not be pharmaceutically active, but will be "bioactive" in the sense that it has an effect on the human body. The agent may be used to treat or alter a condition, which may or may not be a pathological, i.e., a disease state. "Drug", "bioactive agent," "preparation," "medicament," "therapeutic agent," "physiological agent" and "pharmaceutical agent" are used interchangeably herein and include substances for use in the diagnosis, cure, mitigation, arrest, treatment or prevention of a condition or disease state or to affect the structure or function of the body. Skin-wellness agents that function to e.g., soften and moisturize are included in this term. The term "treatment" is used broadly to encompass prevention, alteration, cure and control of the condition.

The drug is present in a drug delivery device of the invention in a therapeutically effective amount, i.e., an amount effective to bring about a desired therapeutic result in the treatment of a condition to which the preparation of this invention is to be applied. Effective amount of a drug means a nontoxic but sufficient amount of a drug to provide the selected effect over a specific period of time. The amount that constitutes a therapeutically effective amount varies according to the particular drug incorporated in the device, the condition being treated, any drugs being co-administered with the selected drug, desired duration of treatment, the surface area of the skin over which the device is to be placed, and other components of the drug delivery device. Such an amount is readily determinable by the skilled practitioner.

Drugs that can be included in the carrier of the invention include substances capable of a local or a systemic effect when administered to the skin. While it will be appreciated that the invention enables the administration of drugs containing a reactive functional group, which drugs have heretofore not been able to be administered by the transdermal route using conventional acrylic adhesives, the invention is not limited to the administration of these types of drugs. Other drugs previously administered via the transdermal route using conventional acrylic adhesives, polyisobutylene-based adhesives or silicone adhesives may also be administered using the adhesive of the invention, either alone or in combination with another drug.

Treatment areas where the delivery device of the invention finds use, and examples of pharmaceutical products which can be incorporated in the devices of the invention, include treatment for incontinence (oxybutinin), central nervous system conditions (methylphenidate), hormone therapy and birth control (estradiol, testosterone, progestin, progesterone, levonorgestrel) cardiovascular (nitroglycerin, clonidine) and cardiotonics (e.g., digitalis, digoxin), pain management or anti-inflammatory (fentanyl, lidocaine, diclofenac, flurbiprofen), cosmetic (benzoyl peroxide, salicylic acid, vitamin C, vitamin E, aromatic oils), antinauseants (scopalamine), smoking cessation (nicotine), antiinflammatory conditions, both steroidal (e.g., hydrocortisone, prednisolone, triamcinolone) and nonsteroidal (e.g., naproxen, piroxicam) treatments, antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin), antiprotazoals (e.g., metronidazole), antifungals (e.g. nystatin), calcium channel blockers (e.g. nifedipine, diltiazem), bronchodilators (e.g., theophylline, pirbuterol, salmeterol, isoproterenol), enzyme inhibitors such as collagenase inhibitors, protease inhibitors, elastase inhibitors, lipoxygenase inhibitors, and angiotensin converting enzyme inhibitors (e.g., captopril, lisinopril), other antihypertensives (e.g., propranolol), leukotriene antagonists, anti-ulceratives such as H2 antagonists, antivirals and/or immunomodulators (e.g., 1Hisobutyl-1H-imidazo[4,5-c]quinolin-4-amine, 1-(2-hydroxy-2-methyl-propyl)-1H-imidazo[4,5-c]quinoline-4-amine, and acyclovir), local anesthetics (e.g., benzocaine, propofol), antitussives (e.g., codeine, dextromethorphan), antihistamines (e.g., diphenhydramine, chlorpheniramine, terfenadine), narcotic analgesics (e.g., morphine, fentanyl), cardioactive products such as atriopeptides, anticonvulsants (e.g., carbamazine), immunosuppressives (e.g., cyclosporine), psychotherapeutics (e.g., diazepam), sedatives (e.g., phenobarbital), anticoagulants (e.g., heparin), analgesics (e.g., acetaminophen), antimigrane agents (e.g., ergotamine, melatonin, sumatriptan), antiarrhythmic agents (e.g., flecainide), antiemetics (e.g., metaclopromide, ondansetron), anticancer agents (e.g., methotrexate), neurologic agents such as anxiolytic drugs, hemostatics, anti-obesity agents, and the like, as well as pharmaceutically acceptable salts, esters, solvates and clathrates thereof.

Veterinary drugs may also be conveniently applied using the transdermal drug delivery device of the invention. In addition to many of the above mentioned drugs, which can also be used in veterinary applications, additional examples include e.g., diclazuril and lufenuron.

Agricultural and horticultural agents include, for example orchid growth hormone.

It will be appreciated that transdermal drug delivery in veterinary and horticultural applications enables more exact dosing, and less waste than administration in the foodlirrigation water.

The skin presents a substantial barrier to ingress of foreign substances into the body. The art has recognized that the barrier to the transdermal or percutaneous delivery of drug through the skin can be overcome or reduced by incorporating excipients into the carrier that enhance the rate at which the drug passes, i.e., penetrates, through the skin. Penetration enhancers are well-known in the art. The terms "enhancement", "penetration enhancement," and permeation enhancement" mean an increase in the permeability of a biological membrane, e.g., skin, to a drug, so as to increase the rate at which the drug permeates through the membrane and accelerate drug delivery. These agents are commonly referred to as penetration enhancers, accelerants, adjuvants and absorption promoters, and will be collectively referred to herein as "enhancers".

The drug delivery system of the invention, in addition to the drug, may advantageously also contain an effective amount of a penetration enhancer. An effective amount of a penetration enhancer means an amount that provides a selected increase in membrane permeability, rate of administration and amount of drug.

Some examples of enhancers are polyhydric alcohols such as dipropylene glycol, propylene glycol, and polyethylene glycol; oils such as olive oil, squalene, and lanolin; polyethylene glycol ethers and fatty ethers such as cetyl ether and oleyl ether; fatty acid esters such as isopropyl myristate; fatty acid alcohols such as oleyl alcohol; urea and urea derivatives such as allantoin; polar solvents such as dimethyidecylphosphoxide, methyloctylsulfoxide, dimethyllaurylamide, didecylpyrrolidone, isosorbitol, dimethylacetonide, dimethylsulfoxide, decylmethylsulfoxide, and dimethylformamide; salicylic acid; amino acids; benzyl nicotinate; bile salts; and higher molecular weight aliphatic surfactants such as lauryl sulfate salts. Other agents include oleic and linoleic acids, ascorbic acid, panthenol butylated hydroxytoluene, tocopherol, tocopheryl acetate, tocopheryl lineleate, propyloleate, isopropyl palmitate, oleamide, polyoxyethylene (4) lauryl ether, polyoxyethylene (2) oleyl ether and polyoxyethylene (10) oleyl ether sold under the trademarks Brij 30, 93 and 97 by ICI Americas, Inc., and polysorbate 20 sold under the trademark Tween 20 by ICI Americas, Inc.

Some drugs function as plasticizers in the adhesive because they are soluble to a certain degree in the polymers comprising the adhesive. When a drug or enhancer modifies the adhesive character of the formulated adhesive, it will generally be necessary to reformulate the adhesive to compensate. For drug molecules which are not sufficiently soluble in the polymer system, a co-solvent for the drug can be added. Co-solvents, such as lecithin, retinol derivatives, tocopherol, dipropylene glycol, triacetin, propylene glycol, saturated and unsaturated fatty acids, mineral oil, alcohols, butyl benzylphthalate, and the like are useful depending on the solubility of the drug in the adhesive carrier.

The formulated component of a transdermal patch device may also include, a controlled-viscosity composition, excipients, diluents, emollients, plasticizers, anti-irritants, opacifiers, fillers, such as clay and silica, pigments and mixtures thereof, preservatives, as well as other components or additives that are formulated for maintaining the drug composition in the polymeric layer in a drug transferring relationship with the derma, e.g., skin, as appropriate for specific applications and which is adapted to adhere to the skin at the application site.

The device of the invention is placed on the skin and allowed to remain for a time sufficient to achieve or maintain the intended therapeutic effect. The time that constitutes a sufficient time can be selected by those skilled in the art with consideration of the flux rate of the device of the invention and of the condition being treated.

The transdermal delivery devices of the invention can be made in the form of an article such as a tape, a patch, a sheet, a dressing or any other form known to those skilled in the art. The dosage system may be produced in any desirable unit form. A circular form is convenient as it contains no corners which might be easily detached from the skin. In addition to having various shapes, the dosage units produced may come in various sizes.

Generally the device will be in the form of a patch of a size suitable to deliver a preselected amount of drug through the skin. A surface area in the range of 1 to 200 $cm^2$ is contemplated and preferred sizes are 5, 10, 15, 20, 25 and 30 $cm^2$. The thickness may vary over a wide range, typically from about 1 to about 5 mil, preferably 3 to 4 mil thick. The present invention preferably incorporates enough pharmaceutically active drug to provide efficacy with a dosage system having a 5 $cm^2$ surface area and a thickness of about 3 to 4 mil.

Depending on the design of the patch and the condition to be treated, the patch will remain on the skin for up to an hour or more, up to about one week. In a preferred embodiment, the patch is designed to remain on the skin at the application site for about 24 hours, and to be changed daily. Preferably, the patch will be placed on the skin at a site different from the location of the previously used patches.

A drug delivery device of the invention can be prepared by using conventional methods to apply an appropriate carrier to the backing. For example, a matrix device can be manufactured by preparing a coating formulation by mixing a solution of the adhesive in a solvent with the drug and any excipients to form a homogeneous solution or suspension; applying the formulation to a substrate (a backing or a release liner) using well known knife or bar or extrusion die coating methods; drying the coated substrate to remove the solvent; and laminating the exposed surface to a release liner or backing.

The invention will be described further in the following examples, which are included for purposes of illustration and are not intended, in any way, to be limiting of the scope of the invention.

In the examples which follow, unless otherwise specified, all parts are by weight and all temperatures in degree Celsius.

All viscosities were measured using a Brookfield viscometer with a #27 spindle.

EXAMPLES

All the formulations described herein were prepared in a 600 g Brabender mixer with sigma blades. The rubbers and about half the oil in the formulation were added to the bowl preheated to about 325° F. Once homogenous, solid tackifers were added followed by additional oil. The formulations are shown in Table 1 wherein:

Septon 4055 is an SEBPS polymer with styrene end blocks and a hydrogenated isoprene/butadiene mid block available from Kuraray. At 5% by weight in toluene at 30° C. it exhibits a viscosity of 5800 cP.

Kraton G1702 is a diblock copolymer of styrene and hydrogenated isoprene available from Shell Chemical. At 10% by weight in toluene at 25° C. it exhibits a viscosity of 3180 cP.

Kristalex 3085 and 5140 are alpha-methyl stryene/styrene end block resins available from Hercules with softening points of 85° C. and 140° C., respectively.

Regalite R-10 is an aliphatic liquid resin with a softening point of 10° C. available from Hercules.

Luminol T350 is a paraffinic white oil available from Petrocanada.

Kaydol is a napthenic white oil available from Witco.

Escorez 5340, 5400 and 5415 are cycloaliphatic resins available from Exxon Chemical with softening points of 140° C., 103° C. and 118° C., respectively.

Irganox 1010 is a hindered phenol antioxidant available from Ciba-Geigy.

TABLE 1

ADHESIVE FORMULATIONS

| Composition | Comparative Example 1 | Comparative Example 2 | Comparative Example 3 | Example 4 | Example 5 |
|---|---|---|---|---|---|
| Septon 4055 | 5 | 5 | 5 | 5 | 5 |
| Kraton G1702 | 5 | 5 | 5 | 5 | 5 |
| Kristalex 3085 | 15 | 15 | — | 15 | 15 |
| Kristalex 5140 | — | — | 5 | — | — |
| Regalite R-10 | 65 | 40 | — | — | — |
| Luminol T350 | — | 20 | — | 40 | 45 |
| Kaydol | — | — | 65 | — | — |
| Escorex 5340 | — | — | 25 | — | — |
| Escorex 5400 | 15 | — | — | — | — |
| Escorex 5415 | — | 20 | — | 40 | 35 |
| Iganox 1010 | 0.5 | 0.5 | 0.5 | 0.5 | 0.5 |

Test Procedures

A Rheometrics Dynamic Mechanical Analyzer (Model RDA 700) was used to obtain the elastic (G') and loss (G") moduli versus temperature. The instrument was controlled by Rhios software version 4.3.2. Parallel plates 8 mm in diameter and separated by a gap of about 2 mm were used. The sample was loaded and then cooled to about −100° C. and the time program started. The program test increased the temperature at 5° C. intervals followed by a soak time at each temperature of 10 seconds. The convection oven containing the sample was flushed continuously with nitrogen. The frequency was maintained at 10 rad/s. The initial strain at the start of the test was 0.05% (at the outer edge of the plates). An autostrain option in the software was used to maintain an accurately measurable torque throughout the test. The option was configured such that the maximum applied strain allowed by the software was 80%. The autostrain program adjusted the strain at each temperature increment if warranted using the following procedure. If the torque was below 200 g-cm the strain was increased by 25% of the current value. If the torque was above 1200 g-cm it was decreased by 25% of the current value. At torques between 200 and 1200 g-cm no change in strain was made at that temperature increment. The shear storage or elastic modulus (G') and the shear loss modulus (G") are calculated by the software from the torque and strain data. Their ratio, G"/G', also known as the tan delta, was also calculated.

The mid block Tg was taken as the maximum in tan delta.

Tensile strength was determined on 0.125" thick, 2.5" long dogbone shaped portions with 1"×1" end tabs and a 0.5"×0.5" central gage portion. These were pulled on an Instron with pneumatic grips at a speed of 20"/min. Strength was taken as the maximum stress during the test.

Two mil thick adhesive drawdowns were made on 1.5 mil polyester backing film. These were used to conduct loop tack tests using a TMI loop tack tester on stainless steel plates.

Peel tests were conducted by bonding one inch wide strips of adhesive to polished stainless steel using two passes of a 2 kg roller. After a 20 minute dwell time the adhesive strips were pulled at 2 inches/minute on an Instron and the average peel force recorded.

Ghosting consists of residue left by the adhesive on the stainless steel plates after the peel test. These determinations were qualitative.

The adhesive properties of the resulting formulation are shown in Table 2.

TABLE 2

ADHESIVE PROPERTIES

| Property | Comparative Example 1 | Comparative Example 2 | Comparative Example 3 | Example 4 | Example 5 |
|---|---|---|---|---|---|
| Viscosity (cP) | | | | | |
| @275° F. | 299,500 | 321,000 | — | 229,000 | — |
| @325° F. | 10,900 | 10,525 | 18,400 | 9,050 | 4,438 |
| Loop tack (oz/in$^2$) | 107 ± 8 | 68 ± 4 | 9 ± 1 | 64 ± 4 | 53 ± 8 |
| Peel (g/in) | 1370 ± 110 | 345 ± 25 | 10 ± 1 | 401 ± 39 | 172 ± 12 |
| Ghosting (residue) | Heavy | Heavy | Trace | Light | Trace |
| G' (10$^4$ dynes/cm$^2$; 25° C.) | 16.1 | 9.4 | 6.1 | 11.4 | 7.4 |
| G" (10$^4$ dynes/cm$^2$; 25° C.) | 15.7 | 4.0 | 1.6 | 4.3 | 2.3 |
| Tan delta (25° C.) | 1.0 | 0.4 | 0.3 | 0.4 | 0.3 |
| Midblock Tg (° C.) | 6 | −6 | −32 | −6 | −8 |

Comparative Example 1 demonstrates that an adhesive with a high level of liquid tackifer and a G' and G" outside the preferred range exhibits peel which is too high for skin contact applications(preferred peel values should be less that 1000 grams) and heavy residue.

Comparative Examples 2 and 3 demonstrate that an adhesive corresponding closely to prior art U.S. Pat. No. 5,559,165. In Comparative Example 2, the majority of the liquid diluent is tackifier rather than oil. Comparative Examples 2 and 3 exhibit either high residue with good peel and tack or minimal residue with peel and tack that is too low.

The adhesives of Examples 4 and 5, prepared in accordance with the invention, show good peel (>100 grams) and tack (>20 oz/in$^2$), exhibit good cohesive strength and leave minimal residue.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

I claim:

1. An pressure sensitive hot melt adhesive composition comprising a high molecular weight rubber and less than about 60 parts by weight of a liquid diluent, and having a G' of less than 15×10$^4$ dynes/cm$^2$ at 10 rad/s at 25° C.

2. The adhesive of claim 1 comprising from about 1 to about 20 parts by weight of a rubber triblock or radial block copolymer, from 0 to about 20 parts by weight of a high molecular weight diblock rubber, 0 to about 10 parts by weight of other compatible high molecular weight polymers, 0 to about 30 parts by weight of an end block resin, 0 to less that 60 parts by weight oil or other liquid midblock diluent, 0 to about 50 parts by weight of a solid tackifer and 0 to about 3 parts by weight of an anti-oxidant.

3. The adhesive of claim 1 having a peel force of greater than about 100 grams per inch.

4. The adhesive of claim 3 having a peel force of from about 100 grams to about 500 grams per inch.

5. The adhesive of claim 1 which has a mid-block Tg of from about −30° C. to about 10° C.

6. The adhesive of claim 2 wherein the triblock copolymer is styrene-(ethylene-butylene)-styrene.

7. The adhesive of claim 2 wherein the triblock copolymer is styrene-(ethylene-butylene-propylene)-styrene.

8. The adhesive of claim 2 which contains an A-B diblock polymer.

9. The adhesive of claim 8 wherein the diblock copolymer is a styrene-(ethylene-propylene) diblock polymer.

10. The adhesive of claim 2 containing an endblock resin.

11. The adhesive of claim 10 wherein the endblock resin is a homo or copolymer of vinyl toluene, styrene, alpha-methyl styrene, coumarone or indene.

12. The adhesive of claim 1 wherein the liquid diluent is present in an amount of from about 35 to about 55 parts by weight.

13. The adhesive of claim 1 wherein the liquid diluent is oil.

14. The adhesive of claim 1 further comprising a therapeutic agent.

15. The adhesive of claim 14 wherein the therapeutic agent is a pharmacologically active agent.

16. A transdermal drug delivery system comprising the adhesive of claim 14.

17. The transdermal drug delivery system of claim 16 wherein the adhesive serves as a carrier for the therapeutic agent.

18. The transdermal drug delivery system of claim 16 comprising an adhesive layer, and a backing layer.

19. The transdermal drug delivery system of claim 18 further comprising a release layer.

20. A method of administering a therapeutic agent to a patient comprising applying to a body surface of a patient a transdermal drug delivery system comprising the adhesive of claim 14 and a therapeutic agent.

* * * * *